United States Patent
Shimada et al.

(10) Patent No.: US 11,103,543 B2
(45) Date of Patent: Aug. 31, 2021

(54) COMPOSITION FOR RECOVERING FROM FATIGUE AND/OR PREVENTING FATIGUE ACCUMULATION

(71) Applicant: Kirin Holdings Kabushiki Kaisha, Tokyo (JP)

(72) Inventors: Kazunori Shimada, Tokyo (JP); Kosuke Fukao, Chiba (JP); Yuta Komano, Tokyo (JP); Toshio Fujii, Tokyo (JP)

(73) Assignee: Kirin Holdings Kabushiki Kaisha, Tokyo (JP)

( * ) Notice: Subject to any disclaimer, the term of this patent is extended or adjusted under 35 U.S.C. 154(b) by 29 days.

(21) Appl. No.: 16/617,280

(22) PCT Filed: Feb. 27, 2018

(86) PCT No.: PCT/JP2018/007092
§ 371 (c)(1),
(2) Date: Nov. 26, 2019

(87) PCT Pub. No.: WO2018/220917
PCT Pub. Date: Dec. 6, 2018

(65) Prior Publication Data
US 2021/0128646 A1    May 6, 2021

(30) Foreign Application Priority Data

May 31, 2017 (JP) .............................. JP2017-107479

(51) Int. Cl.
*A61K 35/744* (2015.01)
*A23L 33/135* (2016.01)

(52) U.S. Cl.
CPC .......... *A61K 35/744* (2013.01); *A23L 33/135* (2016.08)

(58) Field of Classification Search
CPC .................................................... A61K 35/744
See application file for complete search history.

(56) References Cited

U.S. PATENT DOCUMENTS

| | | |
|---|---|---|
| 2001/0051152 A1 | 12/2001 | Krueger et al. |
| 2013/0302380 A1 | 11/2013 | Fujiwara et al. |
| 2015/0139970 A1 | 5/2015 | Tategaki et al. |
| 2019/0167622 A1 | 6/2019 | Takasugi et al. |

FOREIGN PATENT DOCUMENTS

| | | | |
|---|---|---|---|
| AU | 2015202755 A1 * | 12/2015 | ........... A61K 31/513 |
| CN | 102488213 A | 6/2012 | |
| JP | 2003-517828 A | 6/2003 | |

(Continued)

OTHER PUBLICATIONS

International Search Report dated May 1, 2018, in PCT/JP2018/007092.

(Continued)

*Primary Examiner* — Rosanne Kosson
(74) *Attorney, Agent, or Firm* — Foley & Lardner LLP

(57) ABSTRACT

An object of the present invention is to provide a novel food material effective for recovering from fatigue and/or preventing fatigue accumulation. The present invention provides a composition for use in recovering from fatigue and/or preventing fatigue accumulation, comprising a *Lactococcus* bacterium as an active ingredient.

11 Claims, 3 Drawing Sheets

(56) References Cited

FOREIGN PATENT DOCUMENTS

| | | |
|---|---|---|
| JP | 2004-254632 A | 9/2004 |
| JP | 2007-077080 A | 3/2007 |
| JP | 2013-017445 A | 1/2013 |
| JP | 2018-012681 A | 1/2018 |
| JP | 2018-023301 A | 2/2018 |
| SG | 11201605881 A | 9/2016 |
| WO | WO 2012/091081 A1 | 7/2012 |
| WO | WO 2014/021205 A1 | 2/2014 |
| WO | WO 2015/111597 A1 | 7/2015 |
| WO | WO 2018/002240 A1 | 1/2018 |

OTHER PUBLICATIONS

Sashihara et al., "Effects of *Lactobacillus gasseri* OLL2809 and α-lactalbumin on university-student athletes: a randomized, double-blind, placebo-controlled clinical trial," Appl. Physiol. Nutr. Metab., 2013, 38:1228-1235.

International Preliminary Report on Patentability dated Dec. 3, 2019, and Written Opinion dated May 1, 2018, in PCT/JP2018/007092, with English translation.

* cited by examiner

US 11,103,543 B2

COMPOSITION FOR RECOVERING FROM FATIGUE AND/OR PREVENTING FATIGUE ACCUMULATION

CROSS-REFERENCE TO RELATED APPLICATION

The present application is the U.S. National Stage of PCT/JP2018/007092, filed Feb. 27, 2018, which enjoys the benefit of priority from the prior Japanese Patent Application No. 2017-107479 filed on May 31, 2017, the entire disclosure of which is incorporated herein by reference.

TECHNICAL FIELD

The present invention relates to a composition for use in recovering from fatigue and/or preventing fatigue accumulation.

BACKGROUND ART

Many people feel fatigue regardless of age or gender and profession. Fatigue is likely to impair QOL and deteriorate the health condition. Therefore, various living improvements for recovering from fatigue and/or preventing fatigue accumulation have been widely advocated. In general, the improvement of sleep, meal and exercise is said to be effective for recovering from fatigue and preventing fatigue accumulation, but it is not easy to practice these improvements every day. A food material effective for recovering from fatigue and preventing fatigue accumulation, if present, can be said to be preferred since people can easily try to recover from fatigue and prevent fatigue accumulation without concerns about side effects.

Food materials of natural origin regarded as being effective for recovering from fatigue and preventing fatigue accumulation have been proposed so far. For example, a composition for use in preventing and treating a feeling of fatigue or malaise, containing an extract of Gao Shan La Gen Cai (*Pegaeophyton scapiflorum* Hook. f. et Thoms. Marq. et Airy-Shaw) (Patent Document 1) is known as a food material of plant origin. Also, an anti-fatigue composition obtained by inoculating *Bacillus natto* into a medium containing rice bran and soybean and fermenting the bacterium (Patent Document 2) and a lactic acid bacterium belonging to *Enterococcus faecium* having a fatigue ameliorating effect (Patent Document 3) are known as food materials of microbial origin. However, the technique described in Patent Document 2 aims at suppressing lactic acid production to suppress the deterioration in exercise performance, i.e., enhancing the endurance during exercise, and is not intended for recovering from fatigue after exercise. The technique described in Patent Document 3 employs the extension of the exercise duration as an index of fatigue, and can be said to ultimately aim at enhancing the endurance during exercise.

REFERENCE LIST

Patent Documents

Patent Document 1: JP 2007-77080 A
Patent Document 2: JP 2013-17445 A
Patent Document 3: WO 2014/021205

SUMMARY OF THE INVENTION

An object of the present invention is to provide a novel food material effective for recovering from fatigue and/or preventing fatigue accumulation.

The present inventors have now found that *Lactococcus lactis* subsp. *lactis* JCM5805, which is one type of *Lactococcus* bacteria, has an effect for recovering from fatigue in humans. The present inventors have also found that this bacterial strain exhibits an effect for recovering from fatigue also in mice. The present invention is based on these findings.

The present invention provides the following inventions.

[1] A composition for use in recovering from fatigue and/or preventing fatigue accumulation (hereinafter referred to as the "composition of the present invention" in some cases) and an anti-fatigue agent (hereinafter referred to as the "agent of the present invention" in some cases), each comprising a *Lactococcus* bacterium as an active ingredient.

[2] The composition and agent according to [1], wherein the *Lactococcus* bacterium is *Lactococcus lactis*.

[3] The composition and agent according to [1] or [2], wherein the *Lactococcus* bacterium is *Lactococcus lactis* subsp. *lactis* JCM5805.

[4] The composition and agent according to any one of [1] to [3], wherein the fatigue is physical fatigue.

[5] The composition and agent according to any one of [1] to [4], wherein the fatigue is accompanied by reduction in blood testosterone concentration.

[6] The composition and agent according to any one of [1] to [5], which are each used for suppressing the physical fatigue at the time of fatigue accumulation.

[7] The composition and agent according to any one of [1] to [6], which each comprise an effective daily intake amount for humans of the *Lactococcus* bacterium.

[8] The composition and agent according to [7], wherein the effective daily intake amount for humans ranges from 0.5 to 1000 mg as dry bacterial cells.

[9] The composition and agent according to [7], wherein the effective daily intake amount for humans ranges from 5 to 1000 mg as dry bacterial cells.

[10] The composition and agent according to [7], wherein the effective daily intake amount for humans ranges from $1 \times 10^9$ to $2 \times 10^{13}$ as the number of bacterial cells.

[11] The composition and agent according to [7], wherein the effective daily intake amount for humans ranges from $1 \times 10^{10}$ to $2 \times 10^{12}$ as the number of bacterial cells.

[12] The composition and agent according to any one of [1] to [11], which are each in the form of a unit package.

[13] The composition and agent according to any one of [1] to [12], which are each a food composition.

[14] A method for recovering from fatigue and a method for preventing fatigue accumulation, each comprising feeding or administering an effective amount of a *Lactococcus* bacterium to a subject in need thereof.

[15] Use of a *Lactococcus* bacterium for the manufacture of a composition for use in recovering from fatigue and/or preventing fatigue accumulation, for the manufacture of an anti-fatigue agent or an agent for preventing fatigue accumulation, for recovering from fatigue and/or preventing fatigue accumulation, or as an anti-fatigue agent or an agent for preventing fatigue accumulation.

[16] A *Lactococcus* bacterium for use in recovering from fatigue and/or preventing fatigue accumulation.

The composition and agent according to the present invention each comprise, as an active ingredient, a lactic acid bacterium which is a food material that has been eaten by humans for a long time. Accordingly, the composition and agent according to the present invention are advantageous in that they can be used for recovering from fatigue and preventing fatigue accumulation and can be fed over a long time without concerns about side effects.

DETAILED DESCRIPTION OF THE INVENTION

The *Lactococcus* bacterium used as an active ingredient in the present invention is a lactic acid coccus belonging to the genus *Lactococcus*. *Lactococcus* bacteria include *Lactococcus lactis* subsp. *lactis*, *Lactococcus garvieae*, *Lactococcus lactis* subsp. *cremoris* and *Lactococcus lactis* subsp. *hordniae*, and is preferably *Lactococcus lactis* subsp. *lactis*.

Specific examples of *Lactococcus* bacteria include *Lactococcus lactis* subsp. *lactis* JCM5805, *Lactococcus lactis* subsp. *lactis* JCM20101, *Lactococcus lactis* subsp. *lactis* NBRC12007, *Lactococcus lactis* subsp. *lactis* NRIC1150, *Lactococcus garvieae* NBRC100934, *Lactococcus lactis* subsp. *cremoris* JCM16167, *Lactococcus lactis* subsp. *cremoris* NBRC100676, *Lactococcus lactis* subsp. *hordniae* JCM1180, and *Lactococcus lactis* subsp. *hordniae* JCM11040. *Lactococcus lactis* subsp. *lactis* JCM5805 and *Lactococcus lactis* subsp. *lactis* JCM20101 are preferred, and *Lactococcus lactis* subsp. *lactis* JCM5805 is particularly preferred.

Figure 5:
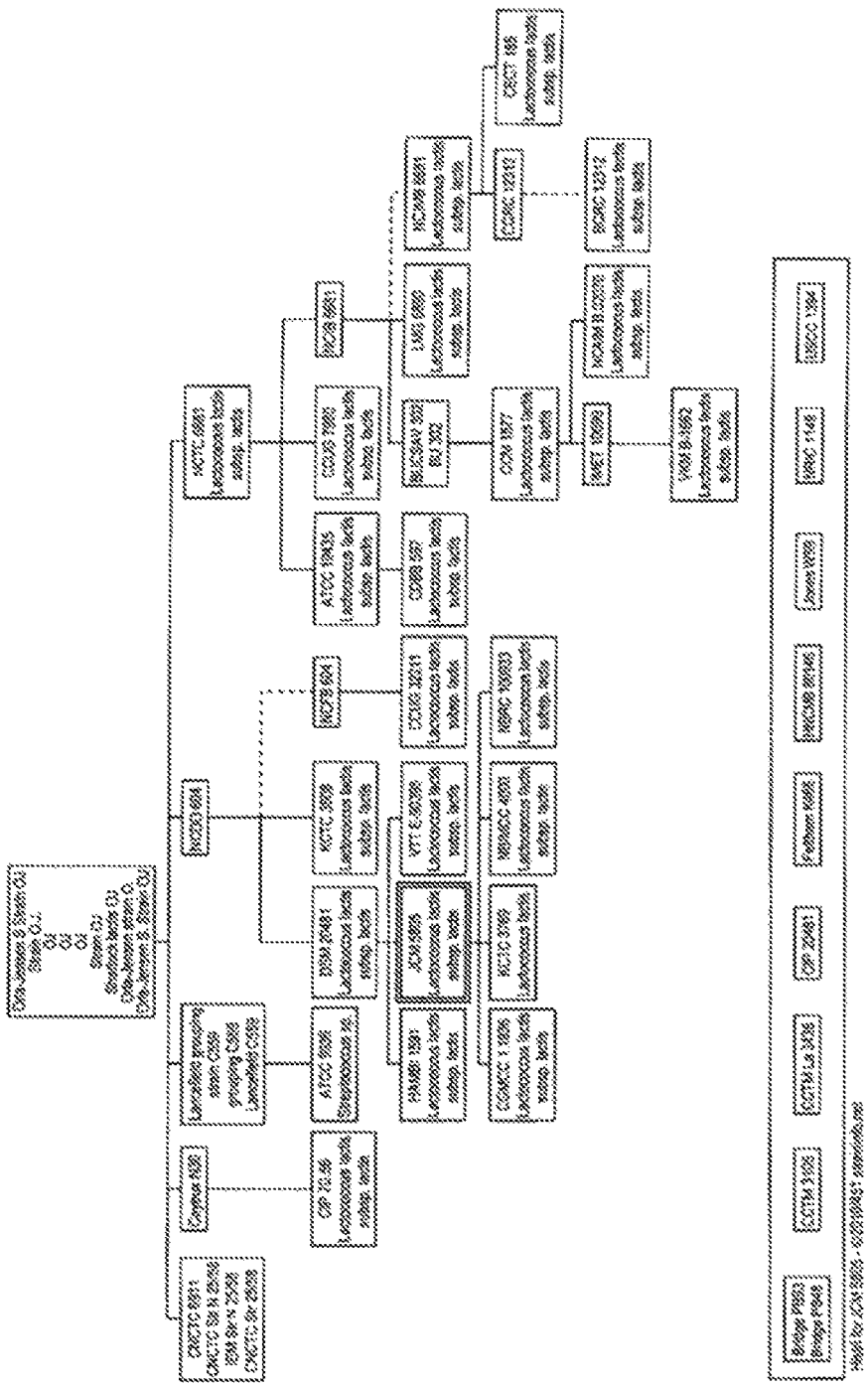
FIG. 5 shows the relationship between *Lactococcus lactis* subsp. *lactis* JCM5805 and a strain equivalent to the JCM5805 strain (a strain derived from the JCM5805 strain and a strain from which the JCM5805 strain is derived).

Among the lactic acid bacterial strains listed above, the JCM bacterial strains are available from the Microbe Division of the RIKEN BioResource Center (http://jcm.brc.riken.jp/ja/); the NBRC bacterial strains are available from the Biological Resource Center (NBRC) at the National Institute of Technology and Evaluation (http://www.nbrc-.nite.go.jp); and the NRIC bacterial strains are available from the Culture Collection Center at Tokyo University of Agriculture (http://nodaiweb.university.jp/nric/). In addition to the specific bacterial strains listed above, bacterial strains equivalent to *Lactococcus lactis* subsp. *lactis* JCM5805, *Lactococcus lactis* subsp. *lactis* JCM20101, *Lactococcus lactis* subsp. *lactis* NBRC12007, *Lactococcus lactis* subsp. *lactis* NRIC1150, *Lactococcus garvieae* NBRC100934, *Lactococcus lactis* subsp. *cremoris* JCM16167, *Lactococcus lactis* subsp. *cremoris* NBRC100676, *Lactococcus lactis* subsp. *hordniae* JCM1180, and *Lactococcus lactis* subsp. *hordniae* JCM11040 can be used in the present invention. The phrase "equivalent bacterial strains," as used herein, refers to bacterial strains derived from the bacterial strains listed above or bacterial strains from which the bacterial strains listed above are derived or offspring bacterial strains of such bacterial strains. Equivalent bacterial strains may be conserved in other culture collection institutes. FIG. 5 shows bacterial strains derived from *Lactococcus lactis* subsp. *lactis* JCM5805 and bacterial strains from which *Lactococcus lactis* subsp. *lactis* JCM5805 is derived. The bacterial strains equivalent to *Lactococcus lactis* subsp. *lactis* JCM5805 shown in FIG. 5 can also be used as the active ingredient of the present invention. "*Lactococcus lactis* subsp. *lactis* JCM5805," as referred to herein, includes these equivalent bacterial strains. Other lactic acid bacteria usable as the active ingredient of the present invention are available from the Microbe Division of the RIKEN BioResource Center (3-1-1 Koyadai, Tsukuba-shi, Ibaraki), American type culture collection (U.S.A.), the National Institute of Technology and Evaluation (2-5-8 Kazusakamatari, Kisarazu-shi, Chiba), the Culture Collection Center at Tokyo University of Agriculture (1-1-1 Sakuragaoka, Setagaya-ku, Tokyo), and the like.

The *Lactococcus* bacterium, which is the active ingredient of the present invention, may be in the form of a culture product. The term "culture product" refers to a live bacterial cell, a dead bacterial cell, a fragmented live or dead bacterial cell, a lyophilized live or dead bacterial cell, or a fragmented product, culture solution or culture extract of such a lyophilized bacterial cell, and include part of *Lactococcus* bacteria and treated products of *Lactococcus* bacteria. Here, such treated products include those obtained by treating *Lactococcus* bacteria with an enzyme, heat and the like and those recovered through ethanol precipitation of such treated products.

*Lactococcus* bacteria can be cultured by a known method using a known medium. Usable media include MRS, GAM and LM17 media, and an inorganic salt, vitamin, amino acid, antibiotic, serum, or the like can be added to such a medium as appropriate. Culturing may sufficiently be carried out at 25° C. to 40° C. for several hours to several days.

After culturing, *Lactococcus* bacterial cells are collected via centrifugation or filtration. When used as dead bacteria, they may be sterilized and inactivated in an autoclave or the like.

The composition and agent according to the present invention can be each provided as the *Lactococcus* bacterium, alone, which is the active ingredient, or can be each provided as a mixture of the *Lactococcus* bacterium which is the active ingredient with any other component (for example, a preparation additive). The amount of the *Lactococcus* bacterium to be blended in the composition and agent according to the present invention can be optionally determined depending, for example, on the purpose, intended use, form, dosage form, symptom, body weight and the like, and can be 0.01% to 99% (w/w), more preferably 10% to 50% (w/w) based on the total amount although the present invention is not limited thereto. In the present invention, the agent of the present invention can consist of a *Lactococcus* bacterium, and the composition of the present invention can comprise a *Lactococcus* bacterium and any other component.

The composition of the present invention is used for recovering from fatigue. The "fatigue," as used herein, means physiological fatigue in healthy persons. Specifically, the "fatigue" can be defined as a state in which the working efficiency (performance) is transiently lowered when mental or physical load is given, including a state in which one has a desire for rest and a state in which one feels discomfort (so called, having a feeling of malaise). Fatigues can be classified into central fatigue caused by imposing load on the brain (for example, mental fatigue) and peripheral fatigue caused by imposing load on the body including muscles (for example, physical fatigue), and the composition and agent according to the present invention can have effect on both the fatigues, but preferably can be used against peripheral fatigue. From the viewpoint of exerting the effect of the present invention better, the fatigue can be physical fatigue (in particular, physical fatigue due to exercise or physical work), especially, physical fatigue at the time of fatigue accumulation, for example, physical fatigue due to practice of exercise for 3 days or more per week or due to continuation of exercise for 3 days or more. Also, according to the present invention, the fatigue can be accompanied by reduction in blood testosterone concentration. It should be noted that the meaning of the "physical fatigue," as used herein, includes exercise fatigue.

In the present invention, the "recovering from fatigue" means alleviation of physiological fatigue. Specifically, the "recovering from fatigue" means that the working efficiency lowered by mental or physical load returns to a normal state, and that the desire for rest and the discomfort are alleviated. Therefore, the meaning of the "recovering from fatigue," as used herein, includes fatigue amelioration and fatigue mitigation.

The composition of the present invention is also used for preventing fatigue accumulation. The "fatigue accumulation," as used herein, means a state in which physiological fatigue caused by single, multiple or continuous load is not alleviated. Specifically, the "fatigue accumulation" means that the working efficiency lowered by mental or physical load does not return to a normal state, and that the desire for rest and the discomfort are continued, and, typically, means physiological fatigue caused by multiple or continuous load. Also, in the present invention, the "preventing fatigue accumulation" means inhibition of a state in which physiological fatigue is not alleviated.

The meaning of the "anti-fatigue agent" of the present invention, includes either or both of a fatigue recovering agent and an agent for preventing fatigue accumulation.

In the present invention, fatigue can be evaluated using animals including humans as test subjects. For example, fatigue in humans can be evaluated based on the evaluation items indicated in the attached table in the "Guideline for Clinical Evaluation of Anti-fatigue (Guideline for Clinical Evaluation Concerning Effect of Anti-fatigue Product against Problematic Fatigue Caused by Daily Life) http://www.hirougakkai.com/guideline.pdf" by the Japanese Society of Fatigue Science and by the VAS inspection method for the feeling of fatigue published in the same society. The fatigue in humans can also be evaluated in the form of a questionnaire which will be described in the Examples later. For the fatigue recovering effect and the fatigue accumulation preventing effect, it can be determined that recovering from fatigue or preventing fatigue accumulation has been successfully achieved in a target for feeding, for example, when the percentage of persons who feel fatigue in a group to which the composition and agent according to the present invention are fed is lower than the percentage of persons who feel fatigue in a group to which a control sample is fed (preferably, when so lower that a significant difference is observed). In the present invention, fatigue can also be evaluated using an animal as a test subject, as will be described in the Examples later.

The composition and agent according to the present invention can be each provided in the form of a pharmaceutical product (for example, pharmaceutical composition), a quasi-drug, a food, a feed or the like, and can be implemented according to the following descriptions.

The *Lactococcus* bacterium which is the active ingredient of the present invention has an effect for recovering from fatigue and/or an effect for preventing fatigue accumulation, and thus can be fed or administered to a fatigued subject or a subject prone to be fatigued. The target for feeding and administration is not limited to a human, and may be an animal other than a human (a horse, a cow, a dog, a cat or the like).

When the *Lactococcus* bacterium which is the active ingredient of the present invention is provided as a food, it can be provided as a food as it is or provided in a state of being contained in a food. The food thus provided is a food containing an effective amount of the active ingredient of the present invention. The phrase "containing an effective amount" of the active ingredient of the present invention refers to a content of the active ingredient to be taken within a range as will be described later, when a normally-eaten amount of individual foods is fed. The meaning of the "food," as used herein, includes health foods, functional foods, nutritional supplements, foods with health claims (such as foods for specified health uses, foods with nutrient function claims, and foods labeled with functions), foods for special dietary uses (such as foods for infants, foods for expectant and nursing mothers and foods for sick persons) and supplements. When the *Lactococcus* bacterium which is the active ingredient of the present invention is fed to an animal other than a human, needless to say, the food referred to herein is used as a feed. Briefly, the meaning of the "food," as used herein, includes "feeds."

The *Lactococcus* bacterium which is the active ingredient of the present invention has an effect for recovering from fatigue and/or an effect for preventing fatigue accumulation, and thus can be contained in foods taken daily or provided as supplements. Briefly, the composition and agent according to the present invention can be each provided in the form of a food. In this case, the composition and agent according to the present invention can be each provided in the form of a unit package in which the intake amount per meal is predetermined. Examples of the unit package form per meal include forms which define a constant amount using a pack, a package, a can, a bottle and the like. To exert various actions of the composition and agent according to the present invention better, the intake amount per meal can be determined according to the intake amount of the *Lactococcus* bacterium per dose which will be described later. The food of the present invention may be provided in the form of a package on which an explanation about the intake amount is given, or provided together with a document or the like which explains the intake amount.

The predetermined intake amount per meal in the unit package form may be either the effective daily intake amount or an intake amount obtained by dividing the effective daily intake amount into two or more (preferably two or three) portions. Thus, the unit package form of the composition and agent according to the present invention can contain the *Lactococcus* bacterium in the daily intake amount for humans which will be described later, or can contain the *Lactococcus* bacterium in an amount half or one third of the daily intake amount for humans which will be described later. For convenience of feeding, the composition and agent according to the present invention are each preferably provided in "the form of a unit package per meal" in which the intake amount per meal is the effective daily intake amount.

The form of the "food" is not particularly limited, and the food may be provided, for example, in a beverage form, in a semi-liquid or gelled form, or in a solid or powder form.

Examples of the "supplement" include tablets manufactured by adding an excipient, a binder and the like to the active ingredient of the present invention, kneading them together and then tableting the kneaded product, and capsule agents in which the active ingredient is encapsulated in a capsule and the like.

The food provided in the present invention is not particularly limited so long as it contains the active ingredient of the present invention, and examples thereof can include non-alcoholic beverages such as refreshing drinks, carbonated drinks, drinks containing fruit juice, drinks containing vegetable juice, drinks containing fruit juice and vegetable juice, cow milk, soybean milk, milk beverages, drink-type yogurt, drink-type jellies, coffee, cocoa, tea drinks, energy drinks, sports drinks, mineral water and flavored water; carbohydrate-containing foods and beverages such as rice, noodles, bread and pasta; various confectioneries such as Western-style confectioneries including cookies, cakes and chocolate, Japanese-style confectioneries including buns with a bean-jam filling and sweet jellies of adzuki beans, candies, gums, yogurt, chilled sweets and frozen sweets including jellies and puddings, and snacks; alcoholic beverages such as whiskey, bourbon, spirit, liqueur, wine, fruit wine, sake (Japanese rice wine), Chinese liquor, shochu (Japanese distilled spirit), beer, non-alcohol beer having an alcohol content of 1% or less, low-malt beer, other miscellaneous liquors and shochu highball; processed products in which eggs are used, processed products of fish and meat (including giblets such as lever) (including rare delicacy), processed foods such as soup, and liquid diets such as high density liquid diets. It should be noted that mineral water includes both of effervescent mineral water and non-effervescent mineral water.

Tea drinks include all of fermented tea, semi-fermented tea and unfermented tea, and examples thereof include black tea, green tea, barley tea, genmai cha (coarse green tea mixed with roasted brown rice), sencha (ordinary green tea), gyokuro cha (refined green tea), hoji cha (roasted green tea), oolong tea, turmeric herbal tea, pu-erth tea, rooibos tea, rose tea, *chrysanthemum* tea, and herb tea (such as mint tea and jasmine tea).

Examples of fruits used in drinks containing fruit juice and drinks containing fruit juice and vegetable juice include apple, orange, grape, banana, pear, peach, mango, acai, blueberry and plum. Examples of vegetables used in drinks containing vegetable juice and drinks containing fruit juice and vegetable juice include tomato, carrot, celery, pumpkin, cucumber and watermelon.

The intake amount of the *Lactococcus* bacterium which is the active ingredient of the present invention can be determined depending, for example, on the sex, age, body weight and symptoms of a target for feeding, feeding time, dosage form, administration route and drug to be combined. When the *Lactococcus* bacterium is fed for the purpose of recovering from fatigue and/or preventing fatigue accumulation, the daily intake amount for humans can be set to, for example 0.5 to 1000 mg or 5 to 1000 mg, preferably 5 to 500 mg, more preferably 10 to 300 mg, further preferably 10 to 100 mg, especially preferably about 50 mg as dry bacterial cells. When the *Lactococcus* bacterium is fed for the purpose of recovering from fatigue and/or preventing fatigue accumulation, the daily intake amount for humans can be set to $1\times10^9$ to $1\times10^{14}$ or $1\times10^9$ to $2\times10^{13}$, preferably $1\times10^{10}$ to $1\times10^{13}$, more preferably $1\times10^{10}$ to $1\times10^{12}$ or $1\times10^{10}$ to $2\times10^{12}$, especially preferably about $1\times10^{11}$ as the number of bacteria. The number of times of feeding is not particularly limited, and the effective intake amount may be fed once daily or fed in several batches. Also, the feeding timing is not particularly limited, and feeding can be performed at a timing when the subject can easily take the *Lactococcus* bacterium. The intake amount and feeding timing of the *Lactococcus* bacterium described above and the feeding period which will be described later are applicable when the *Lactococcus* bacterium which is the active ingredient of the present invention is used for both non-therapeutic and therapeutic purposes, and the "feeding" can be read as "administration" in the case of therapeutic purposes.

The composition and agent according to the present invention can exert the effect better when fed for a long time, and can be continuously fed, for example for 3 days or more, preferably for 6 days or more, more preferably for 10 days or more. The "continuously," as used herein, means that feeding is continued every day. When the composition and agent according to the present invention are each provided in the package form, packages containing an effective intake amount for a certain period (for example, 1 week) may be provided as a set, for continuous feeding.

The composition and agent according to the present invention each utilize, as an active ingredient, a lactic acid bacterium which is a food material which has been eaten by humans for a long time, and thus have high safety without concerns about side effects even when used continuously. Therefore, the combination of the composition and agent according to the present invention with an existing anti-fatigue agent can reduce the dose of the existing agent and therefore can alleviate or overcome the side effects of the existing agent. When used in combination with any other agent, the composition and agent according to the present invention may be prepared separately from the other agent, or the other agent and the composition and agent according to the present invention (or the *Lactococcus* bacterium) may be blended together in the same composition.

The composition and agent as well as food according to the present invention may be attached with an indication that they have an effect for recovering from fatigue and/or an effect for preventing fatigue accumulation. In this case, the composition and agent as well as food according to the present invention may be attached with some or all of the following indications for better understanding of consumers. Needless to say, the meaning of the phrase "recovering from fatigue and/or preventing fatigue accumulation," as used herein, includes the following indications:

facilitating, promoting, enhancing, supporting, ameliorating or improving recovery from fatigue;
facilitating, promoting, enhancing, supporting, ameliorating or improving recovery of feeling of malaise;
maintaining, enhancing, supporting, ameliorating or improving activity;
maintaining, enhancing, supporting, ameliorating or improving condition;
maintaining, enhancing, supporting, ameliorating or improving energy;
maintaining, enhancing, supporting, ameliorating or improving vivacity;
preventing, inhibiting, reducing or suppressing fatigue accumulation;
preventing, inhibiting, reducing or suppressing myalgia;
preventing, inhibiting, reducing or suppressing exhaustion;
preventing, inhibiting, reducing or suppressing wounds all over one's body;
preventing, inhibiting, reducing or suppressing weariness;
preventing, inhibiting, reducing or suppressing languor;
preventing, inhibiting, reducing or suppressing heaviness of body;

preventing, inhibiting, reducing or suppressing hypoactivity; for persons who are anxious about fatigue; and for persons in whom fatigue is easily accumulated.

The indication "after exercise," "after activity," "after physical fatigue" or "during normal time" may be attached to the end of the above indications.

The present invention provides a method for recovering from fatigue and a method for preventing fatigue accumulation, comprising feeding or administering an effective amount of a *Lactococcus* bacterium or a composition comprising the same to a subject in need thereof. The target for feeding or administration is a mammal including a human, preferably a human. The method for recovering from fatigue and method for preventing fatigue accumulation of the present invention and the use of the present invention which will be described later may be use in mammals including humans, and is intended to involve both of therapeutic use and non-therapeutic use. The "non-therapeutic," as used herein, means elimination of operating, treating or diagnosing activities to a human (i.e., medical activities to a human), and specifically means elimination of a method of performing operation or treatment of, or diagnosis involving, a human by a doctor or a person who receives an instruction from the doctor. The method for recovering from fatigue and method for preventing fatigue accumulation according to the present invention can be carried out according to the descriptions about the composition and agent according to the present invention and the active ingredient of the present invention.

The present invention also provides use of a *Lactococcus* bacterium or a composition comprising the same for the manufacture of a composition for use in recovering from fatigue and/or preventing fatigue accumulation. The present invention further provides use of a *Lactococcus* bacterium or a composition comprising the same for the manufacture of an anti-fatigue agent or an agent for preventing fatigue accumulation. The present invention still further provides use of a *Lactococcus* bacterium or a composition comprising the same for recovering from fatigue and/or preventing fatigue accumulation or as an anti-fatigue agent or an agent for preventing fatigue accumulation. The present invention still further provides a *Lactococcus* bacterium or a composition comprising the same for use in recovering from fatigue and/or preventing fatigue accumulation. The use of the present invention and the *Lactococcus* bacterium and composition comprising the same according to the present invention can be implemented according to the descriptions about the composition and agent according to the present invention and the active ingredient of the present invention.

EXAMPLES

Hereinafter, the present invention will be described in more detail by way of the following examples, but is not limited thereto.

Example 1: Effect of Lactic Acid Bacterium (JCM5805) on Promoting Recovery of Feeling of Fatigue in Human (1) Preparation of Lactic Acid Bacterium-Containing Food As a lactic acid bacterium-containing food, a hard capsule No. 3 containing 50 mg ($1.0 \times 10^{11}$ or more) of dry dead bacterial cells of *Lactococcus lactis* subsp. *lactis* JCM5805 (hereinafter referred to as "JCM5805") and 150 mg of corn starch was prepared. As a placebo food, a hard capsule No. 3 containing no JCM5805 and 200 mg of corn starch was prepared.

(2) Test Method

Men of twenty years and over who regularly practiced equivalent exercise at a frequency of five times or more per week were adopted as subjects. Fifty one (51) subjects were randomly divided into two groups without imbalances in age, height, body weight and BMI. The group to which the lactic acid bacterium-containing food was fed was defined as "test group" (26 subjects), and the group to which the placebo food was fed was defined as "control group" (25 subjects). Fifty (50) subjects (test group: 26 subjects and control group: 24 subjects), except 1 subject excluded from the target for analysis, were defined as the target for analysis. The average values±standard deviations of subject information on the respective groups at the beginning of the test are indicated in Table 1.

TABLE 1

| Subject information on the respective groups at the beginning of test | | |
|---|---|---|
| | Test group (n = 26) | Control group (n = 24) |
| Age (years old) | 20.8 ± 0.8 | 20.6 ± 0.8 |
| Height (cm) | 172.2 ± 4.7 | 171.1 ± 6.4 |
| Body weight (kg) | 61.2 ± 6.8 | 60.6 ± 6.5 |
| BMI (kg/m$^2$) | 20.6 ± 1.7 | 20.7 ± 1.6 |

As indicated in Table 1, no significant difference was confirmed between the two groups in terms of the age, height, body weight or BMI at the time of grouping (unpaired t-test).

In a placebo-controlled randomized double blind test design, as test foods, the lactic acid bacterium-containing food prepared in the above item (1) was fed to the test group, whereas the placebo food was fed to the control group. One capsule was continuously fed to the respective groups at an arbitrary timing once daily during the test period (13 days). During the test period, the subjects were made to continue a life habit of practicing regular exercise equivalent to that before the test period, and to record the details and time of the practiced exercise in a subject diary.

During the test period, the subjects were made to evaluate the feeling of fatigue before bedtime every day. Specifically, the subjects were made to select the feeling closest to the feeling of fatigue felt by them from among the following five grades and to record the grade.

1. Feel horrible fatigue
2. Feel considerable fatigue
3. Feel some fatigue
4. Feel slight fatigue
5. Feel no fatigue This test was examined by the "Kirin Internal Ethical Review" and "Ethics Committee of Juntendo University Hospital," obtained approval, and then was conducted. The test was conducted in compliance with the Ethical Principles Based on the Declaration of Helsinki, the Act on the Protection of Personal Information, and "Ethical Guidelines for Epidemiological Research" (Jun. 17, 2002, Ministry of Education, Culture, Sports, Science and Technology and Ministry of Health, Labour and Welfare).

(3) Evaluation Method

The grades "1: Feel horrible fatigue; 2: Feel considerable fatigue and 3: Feel some fatigue" in the records given in the subject diaries were defined as "having feeling of fatigue,"

and the grades "4: Feel slight fatigue and 5: Feel no fatigue" were defined as "having no feeling of fatigue." For each of the groups, obtained was the percentage of the cumulative days for "having feeling of fatigue/having no feeling of fatigue" relative to the cumulative days for the entire test period, which was analyzed by the chi-square test.

Based on the records given in the subject diaries, the daily exercise quantity of each of the subjects was calculated. Here, the exercise quantity was calculated by multiplying the intensity (METs) defining the details of exercise by the exercise time. Specifically, the exercise quantity was calculated by multiplying the daily exercise intensity obtained according to Reference Document 2-2 "Table of METs for Exercise" in the "Report of Review Meeting Concerning Revision of Exercise Standard/Exercise Guidelines" (http://www.mhlw.go.jp/stf/houdou/2r9852000002xple-att/2r9852000002xpqt.pdf) by the exercise time. Based on the records on the details and time of exercise given in the subject diaries, the total sum of exercise quantity for each of the subjects (total exercise quantity for 13 days) was obtained.

(4) Results

Figure 1:
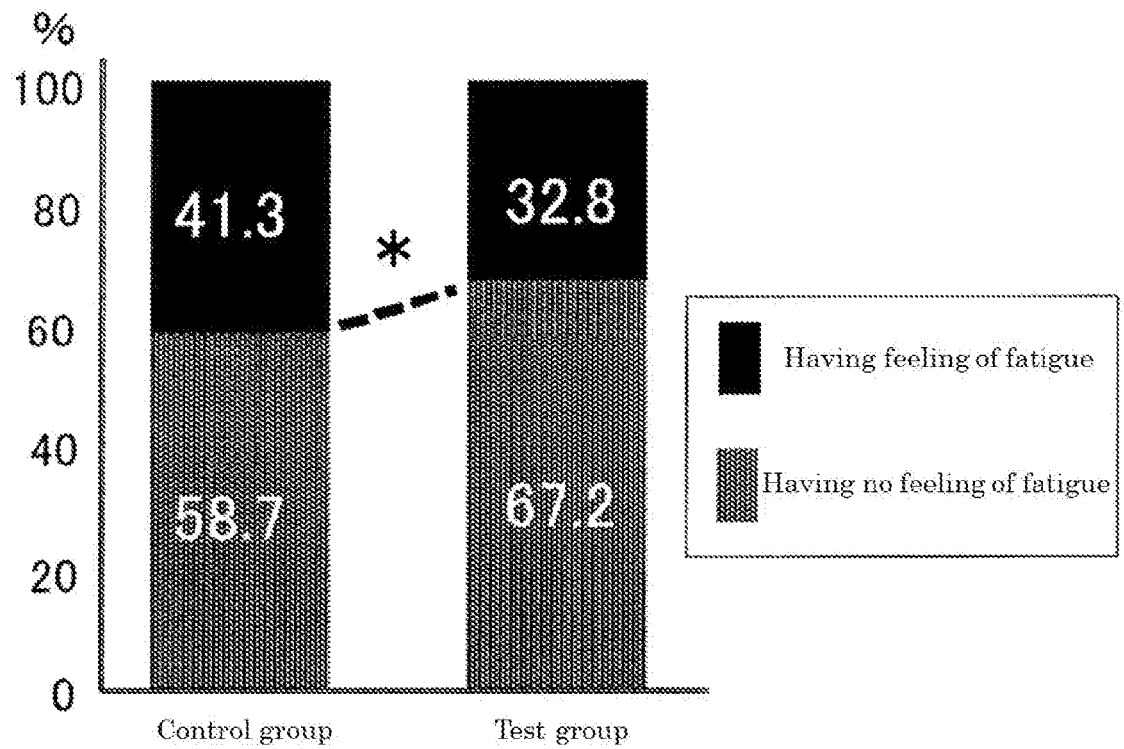
FIG. 1 shows the percentages of cumulative days for a feeling of fatigue. * denotes $p<0.05$ (chi-square test) vs control group.

The results were as shown in FIG. 1. From the results shown in FIG. 1, it was confirmed that the percentage of the cumulative days for "having feeling of fatigue" significantly lowers in the test group to which the lactic acid bacterium (JCM5805)-containing food was fed, as compared with the control group (p<0.05). No significant difference was confirmed between the two groups in terms of the total exercise quantity (METs·hour) for 13 days for each of the subjects during the test period. From the above results, it was confirmed that feeding of the lactic acid bacterium (JCM5805) reduces the feeling of fatigue accumulated by exercise load, i.e., that the lactic acid bacterium (JCM5805)-containing food has the effect of promoting the recovery from fatigue.

Example 2: Effect of Lactic Acid Bacterium (JCM5805) on Improvement of Index of Fatigue in Human (1) Preparation of Lactic Acid Bacterium-Containing Food A lactic acid bacterium-containing food and a placebo food were prepared according to item (1) in Example 1.

(2) Test Method

Men of eighteen years old and over who regularly practiced equivalent exercise at a frequency of four times or more per week were adopted as subjects. Thirty seven (37) subjects were randomly divided into two groups without imbalances in age, height, body weight and BMI. The group to which the lactic acid bacterium-containing food as indicated in Example 1 was fed was defined as "test group" (19 subjects), and the group to which the placebo food was fed was defined as "control group" (18 subjects). Thirty one (31) subjects (test group: 15 subjects and control group: 16 subjects) were defined as the target for analysis. The average values±standard deviations of the subject information on the respective groups at the beginning of the test are indicated in Table 2.

TABLE 2

Subject information on the respective groups at the beginning of test

| | Test group (n = 15) | Control group (n = 16) |
|---|---|---|
| Age (years old) | 19.9 ± 1.2 | 19.8 ± 1.3 |
| Height (cm) | 171.5 ± 5.4 | 171.6 ± 3.7 |

TABLE 2-continued

Subject information on the respective groups at the beginning of test

| | Test group (n = 15) | Control group (n = 16) |
|---|---|---|
| Body weight (kg) | 56.4 ± 4.1 | 56.3 ± 1.8 |
| BMI (kg/m$^2$) | 19.2 ± 1.0 | 19.1 ± 0.9 |

As indicated in Table 2, no significant difference was observed between the two groups in terms of the age, height, body weight or BMI at the time of grouping. (unpaired t-test).

a. Test Schedule

This test was conducted as a placebo-controlled randomized double blind parallel-group comparative test. During the test period (15 days), the subjects were made to do exercise, and to take one capsule containing the test food (test group: lactic acid bacterium-containing food and control group: placebo food), which was the same as that used in Example 1, once daily for the test food feeding period. A specific schedule is as follows.

(i) Test Food Feeding Period

During Day 1 to Day 14 of the test food feeding period, the subjects did exercise in which the exercise quantity was managed by a training coach, and were made to take the test food. During this period, the test food was fed at an arbitrary timing in a day. The exercise quantity in each day was obtained by analyzing the exercise done by each of the subjects, the exercise being described in their diary, by a method similar to that employed in Example 1. The exercise quantity during the test food feeding period was 13.5±3.1 METs·hour/day for the test group and 12.8±2.5 METs·hour/day for the placebo group, and no difference was observed between the two groups.

(ii) Exercise End Date

On Day 15 of the test, the subjects did exercise with a bicycle ergometer for 2 hours under the monitoring of the heart rate. An inspection (blood collection and pulse wave/electrocardiographic wave measurement) was conducted before exercise and at 2 hours after exercise. The average heart rate during exercise was 141.2±9.3 for the test group and 144.7±11.5 for the placebo group, and no difference was observed between the two groups.

b. Inspection Item (i) Testosterone Measurement Through Blood Collection

The testosterone concentration was measured from their sera as samples by the ELISA method (Testosterone Parameter Assay Kit manufactured by R&D Systems, Inc.). It is generally known that the blood testosterone concentration lowers when the feeling of fatigue is strong (Environmental Health and Preventive Medicine, 2: 21-27 (1997)).

(ii) Measurement of Sympathetic Nerve (LF)/Parasympathetic Nerve (HF) Using Pulse Wave/Electrocardiographic Wave The sympathetic nerve (LF)/parasympathetic nerve (HF) ratio, which is evaluated as fatigue stress, was obtained from the pulse wave/electrocardiographic wave. Specifically, for autonomic nerve activities, the frequency spectrum analysis of heart rate variability (HRV) is commonly widely performed. It consists of the two components: low frequency (LF: 0.04 to 0.15 Hz) and high frequency (HF: 0.15 to 0.4 Hz), and it is known that the former component is associated with sympathetic nerve plus parasympathetic nerve functions, and that the latter component is associated with parasympathetic nerve functions (Am. J. Physiol., 248: H151-H153 (1985), Circ. Res., 59: 178-193 (1986)). It is known that a high LF/HF ratio can reflect increased fatigue and that a low LF/HF ratio can reflect reduced fatigue (J. Physiol. Scie., 65: 483-498 (2015)).

In this example, the pulse wave/electrocardiographic wave were measured using an autonomic nerve measurement sensor VM302 (manufactured by Fatigue Science Laboratory Inc., http://www.fatigue.co.jp/pdf/vm302-20170119.pdf). The average value of the LF measured value/HF measured value at every beat within a 90-second measurement time, i.e., LF/HF ratio, was obtained.

This test was examined by the "Kirin Internal Ethical Review" and "Research Ethics Committee of Juntendo University Faculty of Health and Sports Science," obtained approval, and then was conducted. The test was conducted in accordance with the spirits of the Ethical Principles Based on the Declaration of Helsinki, the Act on the Protection of Personal Information, and "Ethical Guidelines for Medical and Health Research" (Dec. 22, 2014 (partially revised on Feb. 28, 2017)).

(3) Evaluation Method

The inspection items were evaluated based on changes in the respective groups (intragroup evaluation) and comparison between the groups (intergroup comparison). Specifically, for the intragroup evaluation for the respective groups, the value 2 hours after exercise relative to the value before exercise on Day 15 of the test (exercise end date) was analyzed by the paired t-test (two-sided test). For the intergroup comparison, the values at each measurement time (before exercise or 2 hours after exercise) for the two groups were analyzed by the unpaired t-test (two-sided test).

(4) Results

Figure 2:
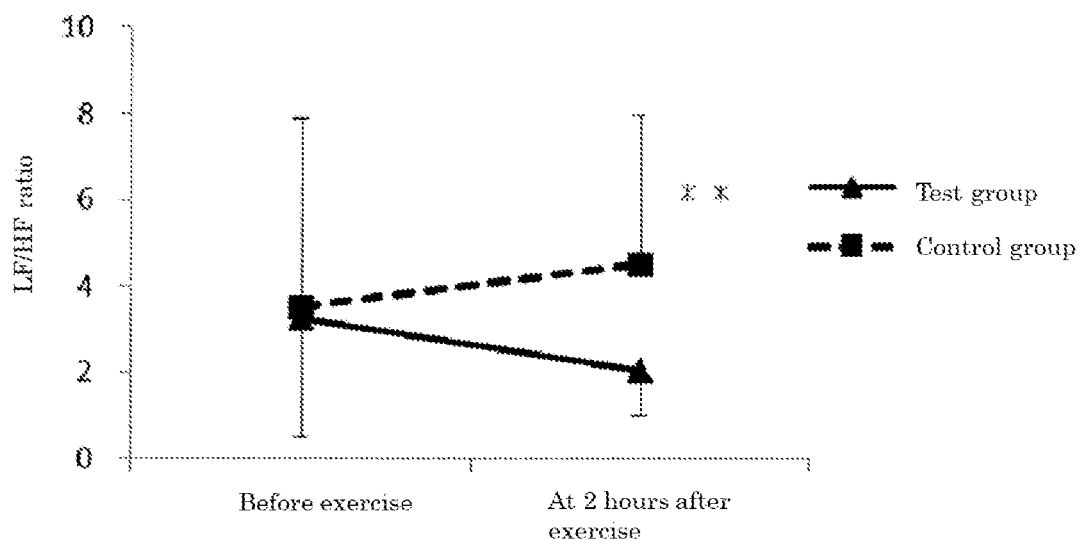
FIG. 2 shows average values of the sympathetic nerve (LF measured value)/parasympathetic nerve (HF measured value) ratios (LF/HF ratios) at every beat within a 90-second measurement time before exercise and after the lapse of 2 hours from exercise for a test group and a control group. ** denotes $p<0.01$ (t-test, two-sided test) vs control group.
Figure 3:
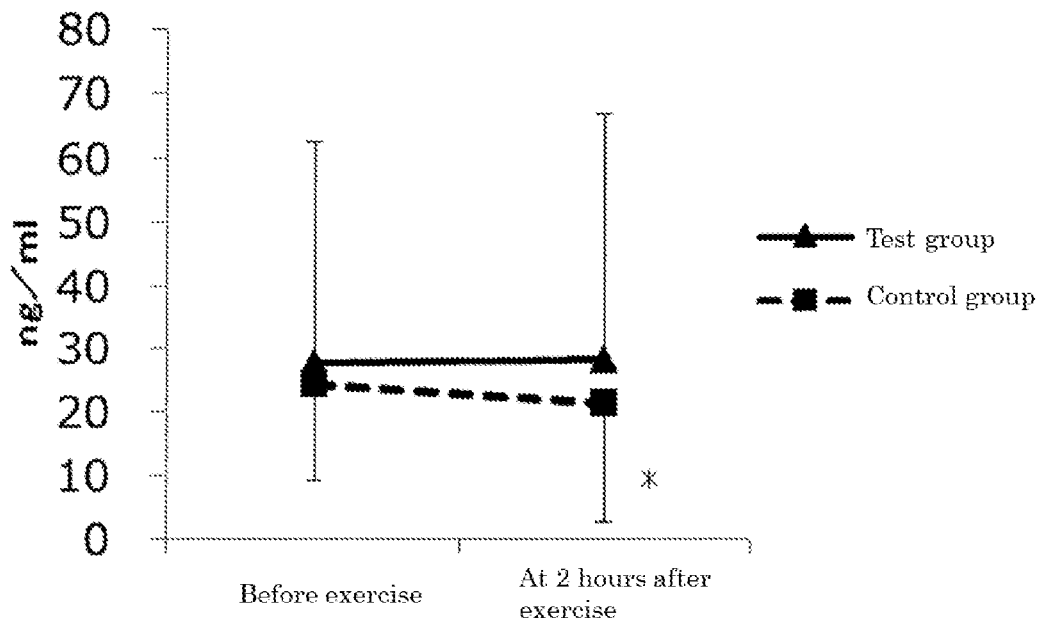
FIG. 3 shows plasma level of testosterone before exercise and after the lapse of 2 hours from exercise for the test group and the control group. * denotes $p<0.05$ (t-test, two-sided test) vs before exercise.

The results were as shown in FIGS. 2 and 3. From the results shown in FIG. 2, the test group to which the lactic acid bacterium (JCM5805)-containing food was fed showed a significantly low LF/HF ratio 2 hours after exercise as compared with the control group (p<0.01). From the results shown in FIG. 3, the serum testosterone concentration on Day 15 of the test was significantly low 2 hours after exercise, as compared with the value before exercise, for the control group (p<0.05), but such an event was not observed in the test group. From the above results, it was confirmed that feeding of the lactic acid bacterium (JCM5805) improves the objective index concerning the fatigue accumulated by exercise load and suppresses exercise fatigue at the time of fatigue accumulation.

Example 3: Effect of Lactic Acid Bacterium (JCM5805) on Promoting Recovery of Feeling of Fatigue in Animal (1) Preparation of Lactic Acid Bacterium-Containing Feed As a lactic acid bacterium-containing feed, a feed mixture in which 0.029% by mass of JCM5805 dry dead bacterial cells were blended in a solid feed AIN-93G (manufactured by Oriental Yeast Co., Ltd.) was prepared. AIN-93G was used as a placebo feed.

(2) Test Method

Four (4)-week-old BALB/c male mice (obtained from Charles River Laboratories) were allowed to freely eat AIN-93G, and acclimated and bred for 7 days. Each 5-week-old mouse after acclimation was transferred to one cage equipped with a rotating basket (product name: RWC-15 manufactured by Melquest Ltd., the same applies hereinafter), allowed to freely eat AIN-93G, and acclimated and bred for 7 days. The 6-week-old mice after acclimation were divided into three groups without imbalances in body weight and quantity of spontaneous exercise in the rotating basket. The group which was fed with the placebo feed and did not practice exercise was defined as "non-exercise load group" (6 mice). The group which was fed with the placebo feed and practiced exercise was defined as "exercise load group" (13 mice). The group which was fed with the lactic acid bacterium-containing feed and practiced exercise was defined as "exercise load/lactic acid bacterium-fed group" (13 mice). The test was started. The average body weight at the beginning of the test (6-week-old) was 21.1±0.8 g for the non-exercise load group, 20.8±0.7 g for the exercise load group, and 20.6±1.1 g for the exercise load/lactic acid bacterium-fed group, and no significant difference was confirmed among the groups (Tukey-Kramer test).

Simultaneously with the beginning of the test, as test feeds, the lactic acid bacterium-containing feed prepared in the above item (1) was freely fed to the exercise load/lactic acid bacterium-fed group, and the placebo feed was freely fed to the non-exercise load group and the exercise load group. The mice were bred for 3 weeks.

Forced walking using a treadmill device as load for causing fatigue in the mice was carried out. Specifically, the 7-week-old mice belonging to the exercise load group and the exercise load/lactic acid bacterium-fed group 1 week after the beginning of feeding the test feeds were made to practice acclimation exercise for forced walking using a treadmill device (product name: MK-680 manufactured by Muromachi Kikai Co., Ltd., the same applies hereinafter) under the conditions indicated in Table 3 every other day for 3 days (for 30 minutes per day).

TABLE 3

| Conditions for acclimation exercise | | | |
|---|---|---|---|
| | Day 1 | Day 2 | Day 3 |
| Slope | 10% | 10% | 10% |
| Running condition | 0-5 min. 5 m/min. 5-20 min. 10 m/min. 20-30 min. 15 m/min. | 0-5 min. 10 m/min. 5-20 min. 15 m/min. 20-30 min. 20 m/min. | 0-5 min. 15 m/min. 5-10 min. 20 m/min. 10-30 min. 25 m/min. |

The 8-week-old mice belonging to the exercise load group and the exercise load/lactic acid bacterium-fed group 2 weeks after the beginning of feeding the test feeds were made to practice the main exercise of forced walking using the treadmill device under the conditions indicated in Table 4 for consecutive 3 days (for 60 minutes per day).

TABLE 4

| Conditions for main exercise | |
|---|---|
| | Days 1 to 3 |
| Slope | 10% |
| Running condition | 0-5 min. 10 m/min. 5-15 min. 15 m/min. 15-60 min. 20 m/min. |

In order to analyze the degree of fatigue of the mice, the spontaneous exercise quantity used as an index of the degree of fatigue of the mice was measured (for example, see Zhang et al. Journal of Neuroinflammation 13: 71 (2016)). As the spontaneous exercise quantity after exercise load, the spontaneous exercise quantity in a dark period (20:00 to 8:00 of the next day) as an active period for the mice was measured for consecutive 3 days after the end of the main exercise for 3 days. Specifically, each mouse was bred in a cage equipped with a rotating basket to measure the spontaneous exercise quantity for 3 days from the day following the end of the main exercise. The spontaneous exercise quantity for the non-exercise load group was measured similarly at the same timing. Also, the spontaneous exercise quantity before exercise load was measured similarly.

(3) Evaluation Method

The recovery rate after exercise load was obtained, based on the following calculation formula, as the percentage of the spontaneous exercise quantity for each of the exercise load group and the exercise load/lactic acid bacterium-fed group to the spontaneous exercise quantity for the non-exercise load group.

Recovery rate (%) after exercise load=spontaneous exercise quantity for exercise load group or exercise load & lactic acid bacterium-fed group/ spontaneous exercise quantity for non-exercise load group×100    [Mathematical Formula 1]

The recovery rates after exercise load for the exercise load group and the exercise load/lactic acid bacterium-fed group were analyzed by the Mann-Whitney U test.

(4) Results

Figure 4:
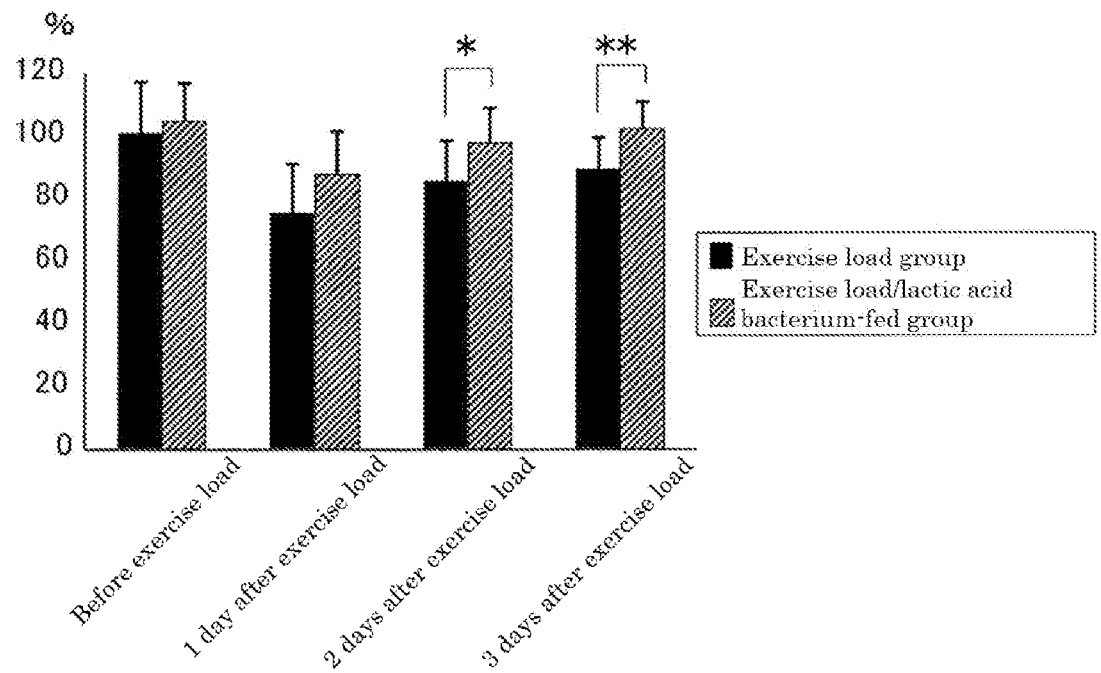
FIG. 4 shows recovery rates before exercise load and after treadmill exercise load. * denotes $p<0.05$ (Mann-Whitney U test) vs exercise load group, and ** denotes $p<0.01$ (Mann-Whitney U test) vs exercise load group.

The results were as shown in FIG. 4. From the results shown in FIG. 4, it was confirmed that the recovery rates after exercise load 2 days and 3 days after exercise load significantly increase in the exercise load/lactic acid bacterium-fed group, as compared with the exercise load group (after 2 days: $p<0.05$ and after 3 days: $p<0.01$). Namely, it was confirmed that feeding of the lactic acid bacterium (JCM5805) leads to recovering from fatigue after treadmill exercise load, i.e., that the lactic acid bacterium (JCM5805)-containing food has the effect of promoting the recovery from fatigue.

The invention claimed is:

1. A method for recovering from fatigue and/or reducing fatigue accumulation, comprising feeding or administering an effective amount of a composition comprising *Lactococcus lactis* subsp. JCM5805 to a subject in need thereof.

2. The method according to claim 1, wherein the fatigue is physical fatigue.

3. The method according to claim 1, wherein the fatigue is accompanied by reduction in blood testosterone concentration.

4. The method according to claim 1, wherein physical fatigue at the time of fatigue accumulation is suppressed.

5. The method according to claim 1, wherein an effective daily intake amount for humans of the *Lactococcus* bacterium is fed or administered.

6. The method according to claim 5, wherein the effective daily intake amount for humans ranges from 0.5 to 1000 mg as dry bacterial cells.

7. The method according to claim 5, wherein the effective daily intake amount for humans ranges from 5 to 1000 mg as dry bacterial cells.

8. The method according to claim 5, wherein the effective daily intake amount for humans ranges from $1\times10^9$ to $2\times10^{13}$ as the number of bacterial cells.

9. The method according to claim 5, wherein the effective daily intake amount for humans ranges from $1\times10^{10}$ to $2\times10^{12}$ as the number of bacterial cells.

10. The method according to claim 1, wherein the *Lactococcus* bacterium is provided in the form of a unit package.

11. The method according to claim 1, wherein the *Lactococcus* bacterium is provided in the form of a food composition.

* * * * *